United States Patent [19]
Yue et al.

[11] Patent Number: 6,004,753
[45] Date of Patent: Dec. 21, 1999

[54] HUMAN S1-5 ECMP-LIKE PROTEIN

[75] Inventors: Henry Yue, Sunnyvale; Karl J. Guegler, Menlo Park; Purvi Shah, Sunnyvale, all of Calif.

[73] Assignee: Incyte Pharmaceuticals, Inc., Palo Alto, Calif.

[21] Appl. No.: 08/980,514

[22] Filed: Dec. 1, 1997

[51] Int. Cl.$^6$ .............................. C12Q 1/68; C12N 15/00; C12N 5/00; C07H 21/02
[52] U.S. Cl. ........................ 435/6; 435/320.1; 435/325; 435/455; 536/23.1
[58] Field of Search .................... 536/23.1; 435/69.1, 435/320.1, 325, 455, 6

[56] References Cited

FOREIGN PATENT DOCUMENTS

WO9738012  10/1997  WIPO .

OTHER PUBLICATIONS

McGowan, S.E. "Extracellular matrix and the regulation of lung development and repair", *FASEB J.*, 6: 2895–2904 (1992).

Grant, D.S. and H.K. Kleinman, "Regulation of capillary formation by laminin and other components of the extracellular matrix", *EXS*, 79: 317–333 (1997).

Taipale, J. and J. Keski–Oja, "Growth factors in the extracellular matrix", *FASEB J.*, 11: 51–59 (1997).

Eleftheriou, C.S. et al., "Cellular ageing related proteins secreted by human fibroblasts", *Mutation Res.*, 256: 127–138 (1991).

Francomano, C.A. et al., "Bone dysplasis in man: molecular insights", *Curr. Opin. Genet. Dev.*, 6: 301–308 (1996).

Pakianathan, D.R. "Extracellular matrix proteins and leukocyte function", *J. Leukocyte Biol.*, 57: 699–702 (1995).

Roman, J. "Extracellular Matrix and Lung Inflammation", *Immunol. Res.*, 15: 163–178 (1996).

Lecka–Czernik, B. et al., "An Overexpressed Gene Transcript in Senescent and Quiescent Human Fibroblasts Encoding a Novel Protein in the Epidermal Growth Factor-Like Repeat Family Stimulates DNA Synthesis", *Mol. Cell. Biol.* 15: 120–128 (1995).

Lecka–Czernik, B. et al., (Direct Submission), GenBank Sequence Database (Accession U03877), National Center for Biotechnology Information, National Library of Medicine, Bethesda, Maryland, 20894, (GI 458227; GI 458228) Apr. 30, 1995.

Chiquet–Ehrismann, R. et al., "Tenascin: an Extracellular Matrix Protein Involved in Tissue Interactions during Fetal Development and Oncogenesis", *Cell*, 47: 131–139 (1986).

*Primary Examiner*—Paula K. Hutzell
*Assistant Examiner*—Lin Sun-Hoffman
*Attorney, Agent, or Firm*—Incyte Pharmaceuticals, Inc; Colette C. Muenzen

[57] ABSTRACT

The invention provides a human S1-5 ECMP-like protein (SELP) and polynucleotides which identify and encode SELP. The invention also provides expression vectors, host cells, antibodies, agonists, and antagonists. The invention also provides methods for treating or preventing disorders associated with expression of SELP.

7 Claims, 7 Drawing Sheets

```
5'                                                                                                        
  G GTG CGA GGA GGT CGA GGA GGC TTG GCA CCC TCT GGC ATC CCG CAC
                                                                    54
    GTC CGA CAT CAG CCC TGC CCT CCT CAG GGG CTT CCA TTC TTG TGC CAA
                                                                   108
    AAG GGA ACT GCC GCC CGT TCT CCG TCT GCC AGG CAT TGC CCA AGC CAG CCG AGC
                                                                   162
    CGC CAG AGC CGC GGG CGG GGG TGT CGC CCC GGG CCC AAC CCC AGG ATG CTC CCC
         Q   S   R   G   R   G   C   R   P   G   P   N   P   R   M   L   P
                                                                   216
    TGC GCC TCC TGC CTA CCC GGG TCT CTA CTG CTC TGG GCG CTG TTG CTC
     C   A   S   C   L   P   G   S   L   L   L   W   A   L   L   L
                                                                   270
    TTG GGA TCA GCT TCT CCT CAG GAT TCT GAA GAG TCT CAG CCC CGA GAA TGC
     L   G   S   A   S   P   Q   D   S   E   E   S   Q   P   R   E   C
                                                                   324
    ACA GAT GGC TAT GAG TGG GAC CCA GAC AGC CAG TGC CAC TGC CGG AAC CAC GAG
     T   D   G   Y   E   W   D   P   D   S   Q   C   H   C   R   N   H   E
                                                                   378
    TGT CTG ATC CCT GAG GCC TGC AAG GGG GAA ATG AAG TGC CGG AAC CAC TAC
     C   L   I   P   E   A   C   K   G   E   M   K   C   I   N   H   Y
                                                                   432
```

FIGURE 1A

```
                            441             450             459             468             477             486
      GGG GGC TAC TTG TGC CTG CCC CGC TCC GCT GCC GTC ATC AAC GAC CTA CAT GGC
       G   G   Y   L   C   L   P   R   S   A   A   V   I   N   D   L   H   G 495             504             513             522             531             540
      GAG GGA CCC CCG CCA CCA GTG CCT CCC GCT CAA CAC CCC AAC CCC TGC CCA CCA
       E   G   P   P   P   P   V   P   P   A   Q   H   P   N   P   C   P   P 549             558             567             576             585             594
      GGC TAT GAG CCC GAC CAG GAC AGC TGT GTG GAT GTG GAC GAG TGT GCC CAG
       G   Y   E   P   D   Q   D   S   C   V   D   V   D   E   C   A   Q 603             612             621             630             639             648
      GCC CTG CAC GAC TGT CGC CCC AGC CAG GAC TGC CAT AAC TTG CCT GGC TCC TAT
       A   L   H   D   C   R   P   S   Q   D   C   H   N   L   P   G   S   Y 657             666             675             684             693             702
      CAG TGC ACC TGC CCT GAT GGT TAC CGC CCC AGC CCC GAG TGT GTG GAC ATA
       Q   C   T   C   P   D   G   Y   R   K   I   G   P   E   C   V   D   I 711             720             729             738             747             756
      GAC TGC TGC CGC TAC TGC CAG CAC CGC TGC GTG AAC CTG CCT GGC TCC
       D   E   C   R   Y   C   Q   H   R   C   V   N   L   P   G   S 765             774             783             792             801             810
      TTC CGC TGC CAG TGC GAG CCG GGC TTC CAG CTG GGG CCT AAC AAC CGC TCC TGT
       F   R   C   Q   C   E   P   G   F   Q   L   G   P   N   N   R   S   C
```

```
      819         828         837         846         855         864
GTT GAT AAC GAG TGT GAC ATG GGG GCC CCA TGC GAG CAG CGC TGC TTC AAC
 V   D   N   E   C   D   M   G   A   P   C   E   Q   R   C   F   N 873         882         891         900         909         918
TCC TAT GGG ACC TTC CTG TGT CGC TGC CAC CAG GGC TAT GAG CTG CAT CGG GAT
 S   Y   G   T   F   L   C   R   C   H   Q   G   Y   E   L   H   R   D 927         936         945         954         963         972
GGC TTC TGC AGT GAT ATT GAT GAG TGT AGC TAC TCC TAC TGC CTC TGT CAG
 G   F   C   S   D   I   D   E   C   S   Y   S   Y   C   L   C   Q 981         990         999        1008        1017        1026
TAC TGC GTC AAC GAG CCA GGC CGT TTC TCC TGC CAC TGC CCA CAG GGT TAC
 Y   R   C   V   N   E   P   G   R   F   S   C   H   C   P   Q   G   Y 1035        1044        1053        1062        1071        1080
CAG CTG CTG GCC ACA CGC CTC TGC CAA GAC ATT GAT GAG TGT GAG TCT GGT GCG
 Q   L   L   A   T   R   L   C   Q   D   I   D   E   C   E   S   G   A 1089        1098        1107        1116        1125        1134
CAC CAG TGC TCC GAG GCC CAA ACC TGT GTC AAC TTC CAT GGG GGC TAC CGC TGC
 H   Q   C   S   E   A   Q   T   C   V   N   F   H   G   G   Y   R   C 1143        1152        1161        1170        1179        1188
GTG GAC ACC AAC CGC TGC GAG CCC TAC ATC CAG GTC TCT GAG AAC CGC TGT
 V   D   T   N   R   C   E   P   Y   I   Q   V   S   E   N   R   C
```

```
     1197       1206       1215       1224       1233       1242
CTC TGC CCG GCC TCC AAC CCT CTA TGT CGA GAG CAG CCT TCA TCC ATT GTG CAC
 L   C   P   A   S   N   P   L   C   R   E   Q   P   S   S   I   V   H 1251       1260       1269       1278       1287       1296
CGC TAC ATG ACC ATC ACC TCG GAG CGG AGC GTG CCC GCT GAC GTG TTC CAG ATC
 R   Y   M   T   I   T   S   E   R   S   V   P   A   D   V   F   Q   I 1305       1314       1323       1332       1341       1350
CAG GCG ACC TCC GTC TAC CCC GGT GCC TAC AAT GCC TTT CAG ATC CGT GCT GGA
 Q   A   T   S   V   Y   P   G   A   Y   N   A   F   Q   I   R   A   G 1359       1368       1377       1386       1395       1404
AAC TCG CAG GGG GAC TTT TAC ATT AGG CAA ATC AAC AAC GTC AGC GCC ATG CTG
 N   S   Q   G   D   F   Y   I   R   Q   I   N   N   V   S   A   M   L 1413       1422       1431       1440       1449       1458
GTC CTC GCC CGG CCG GTG ACG GGC CCC CGG GAG TAC GTG CTG GAC CTG GAG ATG
 V   L   A   R   P   V   T   G   P   R   E   Y   V   L   D   L   E   M 1467       1476       1485       1494       1503       1512
ACC ATG AAT TCC CTC ATG AGC TAC CGG GCC AGC TCT GTA CTG AGG CTC ACC
 T   M   N   S   L   M   S   Y   R   A   S   S   V   L   R   L   T 1521       1530       1539       1548       1557       1566
GTC TTT GTA GGG GCC TAC ACC TTC TGA GGA GCA GGA GGG AGC CAC CCT CCC TGC
 V   F   V   G   A   Y   T   F   *

FIGURE 1D
```

```
            1575        1584        1593        1602        1611        1620
AGC TAC CCT AGC TGA GGA GCC TGT TGT GAG GGG CAG AAT GAG AAA GGC AAT AAA 1629        1638        1647        1656        1665        1674
GGG AGA AAG AAA GTC CTG GTG GCT GAG GTG GGC GGG TCA CAC TGC AGG AAG CCT 1683        1692        1701        1710        1719        1728
CAG GCT GGG GCA GGG TGG CAC TTG GGG CAG GCC AAG TTC ACC TAA ATG GGG 1737        1746        1755        1764        1773        1782
GTC TCT ATA TGT TCA GGC CCA GGG GCC CCC ATT GAC AGG AGC TGG GAG CTC TGC 1791        1800        1809        1818        1827        1836
ACC ACG AGC TTC AGT CAC CCC GAG AGA GGA GGT AAC GAG GAG GGC GGA CTC 1845        1854        1863        1872        1881        1890
CAG GCC CCG GCC CAG AGA TTT GGA CTT GGC TGG CTT GCA GGG GTC CTA AGA AAC 1899        1908        1917        1926        1935        1944
TCC ACT CTG GAC AGC GCC AGG AGG CCC TGG GTT CCA TTC CTA ACT CTG CCT CAA 1953        1962        1971        1980        1989        1998
ACT GTA CAT TTG GAT AAG CCC TAG TAG TTC CCT GGG CCT GTT TTT CTA TAA AAC 2007        2016
GAG GCA ACT GGA AAA AAA AAA A 3'
```

HUMAN S1-5 ECMP-LIKE PROTEIN

FIELD OF THE INVENTION

This invention relates to nucleic acid and amino acid sequences of a human S1-5 ECMP-like protein and to the use of these sequences in the diagnosis, treatment, and prevention of immunological and neoplastic disorders.

BACKGROUND OF THE INVENTION

Many eukaryotic cells are enveloped by an extracellular matrix of proteins that provide structural support, cell and tissue identity, and autocrine, paracrine and juxtacrine properties for the cell within its environment (McGowan, S. E. (1992) FASEB J. 6:2895–2904). The diverse biochemistry of extracellular matrix proteins (ECMP) is indicative of the many, often overlapping, roles that are attributed to each distinct molecule (cf. Grant, D. S. and Kleinman, H. K. (1997) EXS 79:317–333). Whilst a great number of ECMPs have been isolated, it remains unclear how the majority of ECMPs interact with one another or with other molecules residing within the cell membrane. Many ECMPs have been associated with tissue growth and cell proliferation, others with tissue or cell differentiation, and yet others with cell death (cf. Taipale, J. and Keski-Oja, J. (1997) FASEB J. 11:51–59; Eleftheriou, C. S. et al. (1991) Mutat. Res. 256:127–138).

For example, the process of embryonic bone formation involves the creation of an extracellular matrix that mineralizes during the course of tissue maturation. During the life of an individual, this matrix is subject to constant remodeling through the combined actions of osteoblasts (which form mineralized bone) and osteoclasts (which resorb bone). The balance of ECMP composition, and the resulting bone structure, may be perturbed by biochemical changes that result from congenital, epigenetic, or infectious diseases (Francomano, C. A. et al. (1996) Curr. Opin. Genet. Dev. 6:301–308).

ECMPs also act as important mediators and regulators during the inflammatory response. Leukocytes are primed for inflammatory mediator and cytokine production by binding to ECMPs during extravasation (Pakianathan, D. R. (1995) J. Leukoc. Biol. 57:699–702). Deposition of ECMPs is also triggered by inflammation in response to lung injury (Roman, J. (1996) Immunol. Res. 15:163–178). Although the function of newly deposited matrices in injured lungs is unknown, their ability to affect the migration, proliferation, differentiation, and activation state of cells in vitro suggests an important role in the initiation and maintenance of the inflammatory response in vivo (Roman, J. supra)

An example of a recently identified human ECMP which regulates cellular and tissue differentiation is the extracellular protein encoded by the S1-5 gene. S1-5 mRNA is overexpressed both in senescent human fibroblasts established from a subject with Werner syndrome of premature ageing and in growth-arrested normal human fibroblasts (Lecka-Czernik, B. et al. (1995) Mol. Cell. Biol. 15:120–128). The mRNA encodes a 387 amino acid residue protein containing five epidermal growth factor (EGF)-like domains. These domains match the EGF tandem repeat consensus residue sequence within several known extracellular proteins that promote cell growth, development, and cell signaling. The EGF tandem repeat is characterized by a regular distribution of single cysteines. Lecka-Czernik, B. et al. (supra) have suggested that, as occurs with other members of the EGF-like family, the S1-5 gene product may represent a negative and/or positive regulatory factor whose ultimate activity is modulated by the cell environment.

The discovery of a new human S1-5 ECMP-like protein and the polynucleotides encoding it satisfies a need in the art by providing new compositions which are useful in the diagnosis, treatment, and prevention of immunological and neoplastic disorders.

SUMMARY OF THE INVENTION

The invention features a substantially purified polypeptide, human S1-5 ECMP-like protein (SELP), comprising the amino acid sequence of SEQ ID NO: 1 or a fragment of SEQ ID NO: 1.

The invention further provides a substantially purified variant of SELP having at least 90% amino acid identity to the amino acid sequence of SEQ ID NO: 1 or a fragment of SEQ ID NO: 1. The invention also provides an isolated and purified polynucleotide sequence encoding the polypeptide comprising the amino acid sequence of SEQ ID NO: 1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO: 1 or a fragment of SEQ ID NO:1.

Additionally, the invention provides a composition comprising a polynucleotide sequence encoding the polypeptide comprising the amino acid sequence of SEQ ID NO: 1 or a fragment of SEQ ID NO: 1. The invention further provides an isolated and purified polynucleotide sequence which hybridizes under stringent conditions to the polynucleotide sequence encoding the polypeptide comprising the amino acid sequence of SEQ ID NO: 1 or a fragment of SEQ ID NO: 1, as well as an isolated and purified polynucleotide sequence which is complementary to the polynucleotide sequence encoding the polypeptide comprising the amino acid sequence of SEQ ID NO: 1 or a fragment of SEQ ID NO: 1.

The invention also provides an isolated and purified polynucleotide sequence comprising SEQ ID NO:2 or a fragment of SEQ ID NO:2, and an isolated and purified polynucleotide variant having at least 90% polynucleotide identity to the polynucleotide sequence comprising SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO: 1 or a fragment of SEQ ID NO: 1. In another aspect, the expression vector is contained within a host cell.

The invention also provides a method for producing a polypeptide comprising the amino acid sequence of SEQ ID NO: 1 or a fragment of SEQ ID NO: 1, the method comprising the steps of: (a) culturing the host cell containing an expression vector containing at least a fragment of a polynucleotide sequence encoding SELP under conditions suitable for the expression of the polypeptide; and (b) recovering the polypeptide from the host cell culture.

The invention also provides a pharmaceutical composition comprising a substantially purified SELP having the amino acid sequence of SEQ ID NO: 1 or a fragment of SEQ ID NO: 1 in conjunction with a suitable pharmaceutical carrier.

The invention further includes a purified antibody which binds to a polypeptide comprising the amino acid sequence of SEQ ID NO: 1 or a fragment of SEQ ID NO: 1, as well as a purified agonist and a purified antagonist of the polypeptide.

The invention also provides a method for treating or preventing an immunological disorder, the method comprising administering to a subject in need of such treatment an effective amount of an antagonist of SELP.

The invention also provides a method for treating or preventing a neoplastic disorder, the method comprising administering to a subject in need of such treatment an effective amount of an antagonist of SELP.

The invention also provides a method for detecting a polynucleotide encoding SELP in a biological sample containing nucleic acids, the method comprising the steps of:

(a) hybridizing the complement of the polynucleotide sequence encoding the polypeptide comprising SEQ ID NO: 1 or a fragment of SEQ ID NO: 1 to at least one of the nucleic acids of the biological sample, thereby forming a hybridization complex; and (b) detecting the hybridization complex, wherein the presence of the hybridization complex correlates with the presence of a polynucleotide encoding SELP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of SELP. The alignment was produced using MACDNASIS PRO software (Hitachi Software Engineering Co. Ltd., San Bruno, Calif.).

FIGS. 2A and 2B show the amino acid sequence alignments between SELP (2786449; SEQ ID NO: 1) and human S1-5 gene product (GI 458228; SEQ ID NO:3), produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"SELP," as used herein, refers to the amino acid sequences of substantially purified SELP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to SELP, increases or prolongs the duration of the effect of SELP. Agonists may include proteins, nucleic acids, carbohydrates, or any other molecules which bind to and modulate the effect of SELP.

An "allele" or an "allelic sequence," as these terms are used herein, is an alternative form of the gene encoding SELP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding SELP, as described herein, include those sequences with deletions, insertions, or substitutions of different nucleotides, resulting in a polynucleotide the same SELP or a polypeptide with at least one functional characteristic of SELP. Included within this definition are polymorphisms which may or may not be readily detectable using a particular oligonucleotide probe of the polynucleotide encoding SELP, and improper or unexpected hybridization to alleles, with a locus other than the normal chromosomal locus for the polynucleotide sequence encoding SELP. The encoded protein may also be "altered," and may contain deletions, insertions, or substitutions of amino acid residues which produce a silent change and result in a functionally equivalent SELP. Deliberate amino acid substitutions may be made on the basis of similarity in polarity, charge, solubility, hydrophobicity, hydrophilicity, and/or the amphipathic nature of the residues, as long as the biological or immunological activity of SELP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments" refers to fragments of SELP which are preferably about 5 to about 15 amino acids in length and which retain some biological activity or immunological activity of SELP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, for example, Dieffenbach, C. W. and G. S. Dveksler (1995) *PCR Primer, a Laboratory Manual,* Cold Spring Harbor Press, Plainview, N.Y.)

The term "antagonist," as it is used herein, refers to a molecule which, when bound to SELP, decreases the amount or the duration of the effect of the biological or immunological activity of SELP. Antagonists may include proteins, nucleic acids, carbohydrates, antibodies, or any other molecules which decrease the effect of SELP.

As used herein, the term "antibody" refers to intact molecules as well as to fragments thereof, such as Fab, $F(ab')_2$, and Fv fragments, which are capable of binding the epitopic determinant. Antibodies that bind SELP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific DNA or RNA sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic SELP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding SELP or fragments of SELP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding SELP, by northern analysis is indicative of the presence of nucleic acids encoding SELP in a sample, and thereby correlates with expression of the transcript from the polynucleotide encoding SELP.

A "deletion," as the term is used herein, refers to a change in the amino acid or nucleotide sequence that results in the absence of one or more amino acid residues or nucleotides.

The term "derivative," as used herein, refers to the chemical modification of SELP, of a polynucleotide sequence encoding SELP, or of a polynucleotide sequence complementary to a polynucleotide sequence encoding SELP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 10K to 10M in size, and which contain all of the elements required for stable mitotic chromosome segregation and maintenance. (Harrington, J. J. et al. (1997) Nat. Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of SELP. For example, modulation may cause an increase or a decrease in protein activity, binding characteristics, or any other biological, functional, or immunological properties of SELP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.

The term "sample," as used herein, is used in its broadest sense. A biological sample suspected of containing nucleic acids encoding SELP, or fragments thereof, or SELP itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of SELP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human S1-5 ECMP-like protein (SELP), the polynucleotides encoding SELP, and the use of these compositions for the diagnosis, treatment, or prevention of immunological and neoplastic disorders.

Nucleic acids encoding the SELP of the present invention were first identified in Incyte Clone 2786449 from the breast cDNA library (BRSTNOT13) using a computer search for amino acid sequence alignments. A consensus sequence, SEQ ID NO:2, was derived from the following overlapping and/or extended nucleic acid sequences: Incyte Clones 2786449 (BRSTNOT13), 3352713 (PROSNOT28), 440063 (THYRNOTOI), 665441 (SCORNOT01), and 1402624 (LATRTUT02).

In one embodiment, the invention encompasses a polypeptide comprising the amino acid sequence of SEQ ID NO:1, as shown in FIGS. 1A, 1B, 1C, 1D, and 1E. SELP is 443 amino acids in length and has two potential glycosylation sites at residues N-198 and N-394, nine potential casein kinase II phosphorylation sites at residues S-26, S-35, T-60, S-120, T-150, S-200, S-240, S-242, and S-383, four potential protein kinase C phosphorylation sites at residues S-1 83, T-312, S-352, and S-425, a potential signal peptide sequence between residues M-1 and A-25, four potential aspartic acid and asparagine hydroxylation sites between residues C-140 and C-151, C-177 and C-188, C-217 and C-228, and C-258 and C-269, and five EGF-like domains between residues C-109 and C-151, C-1 51 and C-188, C-188 and 228, C-228 and C-269, and C-269 and C-336. As shown in FIGS. 2A and 2B, SELP has chemical and structural homology with human S1-5 gene product (GI 458228; SEQ ID NO:3). In particular, SELP and human S1-5 gene product share 49% identity, one potential N-glycosylation site, one potential casein kinase II phosphorylation site, two potential protein kinase C phosphorylation sites, a potential signal peptide sequence, four potential aspartic acid and asparagine hydroxylation sites, and the five EGF-like domains. In addition, SELP and human S1-5 gene product have rather similar isoelectric points, 4.6 and 5.1, respectively. Northern analysis shows the expression of this sequence in various libraries, at least 69% of which are immortalized or cancerous and at least 21% of which involve the immune response. Of particular note is the expression of SELP in heart, lung, brain, spinal cord, thyroid, breast, prostate, uterus, ovary, penis, gastrointestinal, and bladder tissue, and in smooth muscle, hematopoietic, and rheumatoid tissues.

The invention also encompasses SELP variants. A preferred SELP variant is one having at least about 80%, more preferably at least about 90%, and most preferably at least about 95% amino acid sequence identity to the SELP amino acid sequence.

The invention also encompasses polynucleotides which encode SELP. In a particular embodiment, the invention encompasses a polynucleotide sequence comprising the sequence of SEQ ID NO:2, as shown in FIGS. 1A, 1B, 1C, 1D, and 1E.

The invention also encompasses a variant of a polynucleotide sequence encoding SELP. In particular, such a variant polynucleotide sequence will have at least about 80%, more preferably at least about 90%, and most preferably at least about 95% polynucleotide sequence identity to the polynucleotide sequence encoding SELP. A particular aspect of the invention encompasses a variant of SEQ ID NO:2 which has at least about 80%, more preferably at least about 90%, and most preferably at least about 95% polynucleotide sequence identity to SEQ ID NO:2.

It will be appreciated by those skilled in the art that as a result of the degeneracy of the genetic code, a multitude of polynucleotide sequences encoding SELP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring SELP, and all such variations are to be considered as being specifically disclosed.

Although nucleotide sequences which encode SELP and its variants are preferably capable of hybridizing to the nucleotide sequence of the naturally occurring SELP under appropriately selected conditions of stringency, it may be advantageous to produce nucleotide sequences encoding SELP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding SELP and its derivatives without altering the encoded amino acid sequences include the production of RNA transcripts having more desirable properties, such as a greater half-life, than transcripts produced from the naturally occurring sequence.

The invention also encompasses production of DNA sequences which encode SELP and SELP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding SELP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding SELP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode SELP may be used in recombinant DNA molecules to direct expression of SELP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express SELP.

As will be understood by those of skill in the art, it may be advantageous to produce SELP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter SELP encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding SELP may be ligated to a heterologous sequence to encode a fusion protein. For example, to screen peptide libraries for inhibitors of SELP activity, it may be useful to encode a chimeric SELP protein that can be recognized by a commercially available antibody. A fusion protein may also be engineered to contain a cleavage site located between the SELP encoding sequence and the heterologous protein sequence, so that SELP may be cleaved and purified away from the heterologous moiety.

In another embodiment, sequences encoding SELP may be synthesized, in whole or in part, using chemical methods well known in the art. (See Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of SELP, or a fragment thereof. For example, peptide synthesis can be performed using various solid-phase techniques (Roberge, J. Y. et al. (1995) Science 269:202–204) and automated synthesis may be achieved using the ABI 431A peptide synthesizer (Perkin Elmer).

The newly synthesized peptide may be substantially purified by preparative high performance liquid chromatography. (See, for example, Creighton, T. (1983) *Proteins, Structures and Molecular Principles,* WH Freeman and Co., New York, N.Y.) The composition of the synthetic peptides may be confirmed by amino acid analysis or by sequencing. (See, for example, the Edman degradation procedure described in Creighton, supra.) Additionally, the amino acid sequence of SELP, or any part thereof, may be altered during direct synthesis and/or combined with sequences from other proteins, or any part thereof, to produce a variant polypeptide.

In order to express a biologically active SELP, the nucleotide sequences encoding SELP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding SELP and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual,* Cold Spring Harbor Press, Plainview, N.Y.) and Ausubel, F. M. et al. (1989; *Current Protocols in Molecular Biology,* John Wiley & Sons, New York, N.Y.).

A variety of expression vector/host systems may be utilized to contain and express sequences encoding SELP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding SELP, vectors based on SV40 or EBV may be used with an appropriate selectable marker.

In bacterial systems, a number of expression vectors may be selected depending upon the use intended for SELP. For example, when large quantities of SELP are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding SELP may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae,* a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding SELP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in *McGraw Hill Yearbook of Science and Technology* (1992) McGraw Hill, New York, N.Y.; pp. 191–196.)

An insect system may also be used to express SELP. For example, in one such system, *Autographa californica* nuclear polyhedrosis virus (AcNPV) is used as a vector to express foreign genes in *Spodoptera frugiperda* cells or in Trichoplusia larvae. The sequences encoding SELP may be cloned into a non-essential region of the virus, such as the polyhedrin gene, and placed under control of the polyhedrin promoter. Successful insertion of SELP will render the polyhedrin gene inactive and produce recombinant virus lacking coat protein. The recombinant viruses may then be used to infect, for example, *S. frugiperda* cells or Trichoplusia larvae in which SELP may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding SELP may be ligated into an adenovirus transcription/translation complex consisting of the late promoter and tripartite leader sequence. Insertion in a non-essential E1 or E3 region of the viral genome may be used to obtain a viable virus which is capable of expressing SELP in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6M to 10M are constructed and delivered via conventional delivery methods (liposomes, polycationic amino polymers, or vesicles) for therapeutic purposes.

Specific initiation signals may also be used to achieve more efficient translation of sequences encoding SELP. Such signals include the ATG initiation codon and adjacent sequences. In cases where sequences encoding SELP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing SELP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyl-transferase genes (Lowy, I. et al. (1980) Cell 22:817–23), which can be employed in tk⁻ or apr⁻ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als and pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding SELP is inserted within a marker gene sequence, transformed cells containing sequences encoding SELP can be identified by the absence of marker gene function. Alternatively, a marker gene can be placed in tandem with a sequence encoding SELP under the control of a single promoter. Expression of the marker gene in response to induction or selection usually indicates expression of the tandem gene as well.

Alternatively, host cells which contain the nucleic acid sequence encoding SELP and express SELP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein sequences.

The presence of polynucleotide sequences encoding SELP can be detected by DNA—DNA or DNA-RNA hybridization or amplification using probes or fragments or fragments of polynucleotides encoding SELP. Nucleic acid amplification based assays involve the use of oligonucleotides or oligomers based on the sequences encoding SELP to detect transformants containing DNA or RNA encoding SELP.

A variety of protocols for detecting and measuring the expression of SELP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on SELP is preferred, but a competitive binding assay may be employed. These and other assays are well described in the art, for example, in Hampton, R. et al. (1990; *Serological Methods, a Laboratory Manual,* APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding SELP include oligolabeling, nick translation, end-labeling, or PCR amplification using a labeled nucleotide. Alternatively, the sequences encoding SELP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding SELP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode SELP may be designed to contain signal sequences which direct secretion of SELP through a prokaryotic or eukaryotic cell membrane. Other constructions may be used to join sequences encoding SELP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the SELP encoding sequence may be used to facilitate purification. One such expression vector provides for expression of a fusion protein containing SELP and a nucleic acid encoding 6 histidine residues preceding a thioredoxin or an enterokinase cleavage site. The histidine residues facilitate purification on immobilized metal ion affinity chromatography (IMAC; described in Porath, J. et al. (1992) Prot. Exp. Purif. 3: 263–281)), while the enterokinase cleavage site provides a means for purifying SELP from the fusion protein. A discussion of vectors which contain fusion proteins is provided in Kroll, D. J. et al. (1993; DNA Cell Biol. 12:441–453).

Fragments of SELP may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431 A peptide synthesizer (Perkin Elmer). Various fragments of SELP may be synthesized separately and then combined to produce the full length molecule.

Therapeutics

Chemical and structural homology exists between SELP and human S1-5 gene product (GI 458228; SEQ ID NO:3). In addition, SELP is expressed in tumor and immunological tissues, heart, lung, brain, spinal cord, thyroid, breast, prostate, uterus, ovary, penis, gastrointestinal, and bladder tissue, and in smooth muscle, hematopoietic, and rheumatoid tissues. Therefore, SELP appears to play a role in immunological and neoplastic disorders.

Therefore, in one embodiment, an antagonist of SELP may be administered to a subject to treat or prevent an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds SELP may be used directly as an antagonist or indirectly as a targeting or delivery mechanism for bringing a pharmaceutical agent to cells or tissue which express SELP.

In an additional embodiment, a vector expressing the complement of the polynucleotide encoding SELP may be administered to a subject to treat or prevent an immunological disorder including, but not limited to, those described above.

In a further embodiment, an antagonist of SELP may be administered to a subject to treat or prevent a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds SELP may be used directly as an antagonist or indirectly as a targeting or delivery mechanism for bringing a pharmaceutical agent to cells or tissue which express SELP.

In an additional embodiment, a vector expressing the complement of the polynucleotide encoding SELP may be administered to a subject to treat or prevent a neoplastic disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of SELP may be produced using methods which are generally known in the art. In particular, purified SELP may be used to produce antibodies or to screen libraries of pharmaceutical agents to identify those which specifically bind SELP. Antibodies to SELP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with SELP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to SELP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of SELP amino acids may be fused with those of another protein, such as KLH, and antibodies to the chimeric molecule may be produced.

Monoclonal antibodies to SELP may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce SELP-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for SELP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between SELP and its specific antibody. A two-site, monoclonal-based immunoassay utilizing monoclonal antibodies reactive to two non-interfering SELP epitopes is preferred, but a competitive binding assay may also be employed. (Maddox, supra.)

In another embodiment of the invention, the polynucleotides encoding SELP, or any fragment or complement thereof, may be used for therapeutic purposes. In one aspect, the complement of the polynucleotide encoding SELP may be used in situations in which it would be desirable to block the transcription of the mRNA. In particular, cells may be transformed with sequences complementary to polynucleotides encoding SELP. Thus, complementary molecules or fragments may be used to modulate SELP activity, or to achieve regulation of gene function. Such technology is now well known in the art, and sense or antisense oligonucleotides or larger fragments can be designed from various locations along the coding or control regions of sequences encoding SELP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding SELP. These techniques are described, for example, in Sambrook (supra) and in Ausubel (supra).

Genes encoding SELP can be turned off by transforming a cell or tissue with expression vectors which express high levels of a polynucleotide or fragment thereof encoding SELP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding SELP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches,* Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding SELP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SELP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of SELP, antibodies to SELP, and mimetics, agonists, antagonists, or inhibitors of SELP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0. 1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of SELP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example SELP or fragments thereof, antibodies of SELP, and agonists, antagonists or inhibitors of SELP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio between toxic to therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind SELP may be used for the diagnosis of disorders characterized by expression of SELP, or in assays to monitor patients being treated with SELP or agonists, antagonists, and inhibitors of SELP. Antibodies useful for diagnostic purposes may be prepared in the same manner as those described above for therapeutics. Diagnostic assays for SELP include methods which utilize the antibody and a label to detect SELP in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring SELP, including ELISAs, RIAs, and FACS, are known in the art and provide a basis for diagnosing altered or abnormal levels of SELP expression. Normal or standard values for SELP expression are established by combining body fluids or cell extracts taken from normal mammalian subjects, preferably human, with antibody to SELP under conditions suitable for complex formation The amount of standard complex formation may be quantified by various methods, preferably by photometric means. Quantities of SELP expressed in subject samples from biopsied tissues are compared with the standard values. Deviation between standard and subject values establishes the parameters for diagnosing disease.

In another embodiment of the invention, the polynucleotides encoding SELP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of SELP may be correlated with disease. The diagnostic assay may be used to distinguish between absence, presence, and excess expression of SELP, and to monitor regulation of SELP levels during therapeutic intervention.

In one aspect, hybridization with PCR probes which are capable of detecting polynucleotide sequences, including genomic sequences, encoding SELP or closely related molecules may be used to identify nucleic acid sequences which encode SELP. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding SELP, alleles, or related sequences.

Probes may also be used for the detection of related sequences, and should preferably contain at least 50% of the nucleotides from any of the SELP encoding sequences. The hybridization probes of the subject invention may be DNA or RNA and may be derived from the sequence of SEQ ID NO:2 or from genomic sequences including promoter and enhancer elements and introns of the naturally occurring SELP.

Means for producing specific hybridization probes for DNAs encoding SELP include the cloning of polynucleotide sequences encoding SELP or SELP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding SELP may be used for the diagnosis of a disorder associated with expression of SELP. Examples of such a disorder include an immunological disorder such as, but not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma; and a neoplastic disorder such as, but not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding SELP may be used in Southern or northern analysis, dot blot, or other membrane-based technologies; in PCR technologies; in dipstick, pin, and ELISA assays; and in microarrays utilizing fluids or tissues from patient biopsies to detect altered SELP expression. Such qualitative or quantitative methods are well known in the art.

In a particular aspect, the nucleotide sequences encoding SELP may be useful in assays that detect the presence of associated disorders, particularly those mentioned above. The nucleotide sequences encoding SELP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding SELP in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of SELP, a normal or standard profile for expression is established. This may be accomplished by combining body fluids or cell extracts taken from normal subjects, either animal or human, with a sequence, or a fragment thereof, encoding SELP, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SELP may involve the use of PCR. Such oligomers may be chemically synthesized, generated enzymatically, or produced in vitro. Oligomers will preferably consist of two nucleotide sequences, one with sense orientation (5' to 3') and another with antisense orientation (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of SELP include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding SELP may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding SELP on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11 q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, SELP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between SELP and the agent being tested may be measured.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with SELP, or fragments thereof, and washed. Bound SELP is then detected by methods well known in the art. Purified SELP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SELP specifically compete with a test compound for binding SELP. In this manner, antibodies can be used to detect the presence of any peptide which shares one or more antigenic determinants with SELP.

In additional embodiments, the nucleotide sequences which encode SELP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BRSTNOT13 cDNA Library Construction

The BRSTNOT13 cDNA library was constructed from the left medial breast tissue obtained from a 36-year-old Caucasian female (specimen #0372) during a bilateral simple mastectomy and a total breast reconstruction. Pathology indicated benign breast tissue in the medial section of left breast, right breast, and right high axillary tail. Patient history included a breast neoplasm, depressive disorder, hyperlipidemia, alcohol and tobacco abuse in remission, ectopic pregnancy, and chronic gastric ulcer. Family history included myocardial infarction and atherosclerotic coronary artery disease in the father and a grandparent; cerebrovascular disease and malignant skin neoplasm in the father; hyperlipidemia in the mother, father, and a sibling; alcohol abuse in remission and depressive disorder in a sibling; malignant breast neoplasm in the mother, a sibling and a grandparent; breast cancer (terminal) and Hodgkin's lymphoma in a paternal aunt; esophageal cancer and bone cancer in a paternal uncle; and bladder cancer and a heart condition in a maternal aunt The frozen tissue was homogenized and lysed in TRIZOL reagent (1 g tissue/10 ml TRIZOL reagent; Cat. #10296-028; GIBCO-BRL, Gaithersburg, Md.), a monophasic solution of phenol and guanidine isothiocyanate, using a Polytron PT-3000 homogenizer (Brinkmann Instruments, Westbury, N.Y.). After a brief incubation on ice, chloroform was added (1:5 v/v), and the lysates were centrifuged. The upper chloroform layer was removed to a fresh tube, and the RNA extracted with isopropanol, resuspended in DEPC-treated water, and treated with DNase for 25 min at 37° C. The mRNA was precipitated using 0.3M sodium acetate and 2.5 volumes ethanol. Extraction and precipitation of mRNA were repeated as before. The mRNA was then isolated using the OLIGOTEX kit (QIAGEN, Inc., Chatsworth, Calif.) and used to construct the cDNA library.

The mRNA was handled according to the recommended protocols in the SUPERSCRIPT plasmid system (Cat. #18248-013, GIBCO-BRL). cDNA synthesis was initiated with aNotI-oligo d(T) primer. Double-stranded cDNA was blunted, ligated to EcoRI adaptors, digested with NotI, fractionated on a SEPHAROSE CL4B column (Cat. #275105-01; Pharmacia), and those cDNAs exceeding 400 bp were ligated into the NotI and EcoRi sites of the pINCY 1 vector (Incyte). The plasmid pINCY 1 was subsequently transformed into DH5α competent cells (Cat. #18258-012; GIBCO-BRL).

II Isolation and Sequencing of cDNA Clones

Plasmid DNA was released from the cells and purified using the R.E.A.L. PREP 96 plasmid kit (Catalog #26173; QIAGEN, Inc.). The recommended protocol was employed except for the following changes: 1) the bacteria were cultured in 1 ml of sterile Terrific Broth (Catalog #22711, GIBCO-BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.) and ABI 377 DNA sequencing systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol. 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra).

Analogous computer techniques applying BLAST are used to search for identical or related molecules in nucleotide databases such as GenBank or the LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding SELP occurs. Abundance and percent abundance are also reported. Abundance directly reflects the number of times a particular transcript is represented in a cDNA library, and percent abundance is abundance divided by the total number of sequences examined in the cDNA library.

V. Extension of SELP Encoding Polynucleotides

The nucleic acid sequence of Incyte Clone 2786449 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M.J. Research, Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (Sambrook, supra). After incubation for one hour at 37° C., the E. coli mixture was plated on Luria Bertani (LB) agar (Sambrook, supra) containing 2x Carb. The following day, several colonies were randomly picked from each plate and cultured in 150 μl of liquid LB/2x Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified using a SEPHADEX G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.), hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequence complementary to the SELP-encoding sequence, or any part thereof, is used to detect, decrease, or inhibit expression of naturally occurring SELP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of SELP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the SELP-encoding transcript.

IX. Expression of SELP

Expression of SELP is accomplished by subcloning the cDNAs into appropriate vectors and transforming the vectors into host cells. In this case, the cloning vector is also used to express SELP in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropylthiogalactoside (IPTG) using standard methods produces a fusion protein which consists of the first 8 residues of β-galactosidase, about 5 to 15 residues of linker, and the full length protein. The signal residues direct the secretion of SELP into bacterial growth media which can be used directly in the following assay for activity.

X. Demonstration of SELP Activity

The activity of human S1-5 ECMP-like protein may be measured using an assay based upon the property of ECMPs to support in vitro proliferation of fibroblasts and tumor cells under serum-free conditions (Chiquet-Ehrismann, R. et al. (1986) Cell 47:131–139). Wells in 96 well cluster plates (Falcon, Fisher Scientific, Santa Clara, Calif.) are coated with SELP by incubation with solutions at 50–100 µg SELP/ml for 15 min at ambient temperature. The coating solution is aspirated, and the wells washed with Dulbecco's medium before cells are plated. Rat fibroblast cultures or rat mammary tumor cells are prepared as described (Chiquet-Ehrismann, R. et al. (1986) supra) and plated at a density of $10^4$–$10^5$ cells/ml in Dulbecco's medium supplemented with 10% fetal calf serum.

After three days the medium is removed, and the cells washed three times with phosphate-buffered saline (PBS), pH 7.0, before addition of serum-free Dulbecco's medium containing 0.25 mg/ml bovine serum albumin (BSA, Fraction V, Sigma Chemical Company, St. Louis, Mo.). After 2 days the medium is aspirated, and 100 µl of [3H]thymidine (NEN) at 2 µCi/ml in fresh Dulbecco's medium containing 0.25 mg/ml BSA is added. Parallel plates are fixed and stained to determine cell numbers. After 16 hr, the medium is aspirated, the cell layer washed with PBS, and the 10% trichloroacetic acid-precipitable radioactivity in the cell layer determined by liquid scintillation counting (normalized to relative cell numbers; Chiquet-Ehrismann, R. et al. (1986) supra).

XI. Production of SELP Specific Antibodies

SELP substantially purified using PAGE electrophoresis (Sambrook, supra), or other purification techniques, is used to immunize rabbits and to produce antibodies using standard protocols. The SELP amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel (supra) and by others.

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring SELP Using Specific Antibodies

Naturally occurring or recombinant SELP is substantially purified by immunoaffinity chromatography using antibodies specific for SELP. An immunoaffinity column is constructed by covalently coupling SELP antibody to an activated chromatographic resin, such as CNBr-activated SEPHAROSE (Pharmacia & Upjohn). After the coupling, the resin is blocked and washed according to the manufacturer's instructions.

Media containing SELP are passed over the immunoaffinity column, and the column is washed under conditions that allow the preferential absorbance of SELP (e.g., high ionic strength buffers in the presence of detergent). The column is eluted under conditions that disrupt antibody/SELP binding (e.g., a buffer of pH 2 to pH 3, or a high concentration of a chaotrope, such as urea or thiocyanate ion), and SELP is collected.

XIII. Identification of Molecules Which Interact with SELP

SELP or biologically active fragments thereof are labeled with $^{125}$I Bolton-Hunter reagent. (Bolton et al. (1973) Biochem. J. 133:529.) Candidate molecules previously arrayed in the wells of a multi-well plate are incubated with the labeled SELP, washed, and any wells with labeled SELP complex are assayed. Data obtained using different concentrations of SELP are used to calculate values for the number, affinity, and association of SELP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide consisting of SEQ ID NO:2.

2. A composition comprising the polynucleotide of claim 1.

3. An isolated and purified polynucleotide which is fully complementary to the polynucleotide of claim 1.

4. An expression vector containing the polynucleotide of claim 1.

5. A host cell containing the expression vector of claim 4.

6. A method for detecting a polynucleotide consisting of SEQ ID NO:2 in a biological sample containing nucleic acids, the method comprising the steps of:

(a) hybridizing the polynucleotide of claim 3 to at least one of the nucleic acids of the biological sample, thereby forming a hybridization complex; and (b) detecting the hybridization complex, wherein the presence of the hybridization complex correlates with the presence of the polynucleotide comprising SEQ ID NO:2 in the biological sample.

7. The method of claim 6 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 443 amino acids
        (B) TYPE: amino acid
        (C) STRANDEDNESS: single
        (D) TOPOLOGY: linear (vii) IMMEDIATE SOURCE:
        (A) LIBRARY: BRSTNOT13
        (B) CLONE: 2786449

(xi) SEQUENCE DESCRIPTION: SEQ ID NO:1:

```
Met Leu Pro Cys Ala Ser Cys Leu Pro Gly Ser Leu Leu Leu Trp Ala
1               5                   10                  15

Leu Leu Leu Leu Leu Leu Gly Ser Ala Ser Pro Gln Asp Ser Glu Glu
            20                  25                  30

Pro Asp Ser Tyr Thr Glu Cys Thr Asp Gly Tyr Glu Trp Asp Pro Asp
            35                  40                  45

Ser Gln His Cys Arg Asp Val Asn Glu Cys Leu Thr Ile Pro Glu Ala
        50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95

Pro Pro Pro Val Pro Pro Ala Gln His Pro Asn Pro Cys Pro Pro Gly
            100                 105                 110

Tyr Glu Pro Asp Asp Gln Asp Ser Cys Val Asp Val Asp Glu Cys Ala
            115                 120                 125

Gln Ala Leu His Asp Cys Arg Pro Ser Gln Asp Cys His Asn Leu Pro
        130                 135                 140

Gly Ser Tyr Gln Cys Thr Cys Pro Asp Gly Tyr Arg Lys Ile Gly Pro
145                 150                 155                 160

Glu Cys Val Asp Ile Asp Glu Cys Arg Tyr Arg Tyr Cys Gln His Arg
                165                 170                 175

Cys Val Asn Leu Pro Gly Ser Phe Arg Cys Gln Cys Glu Pro Gly Phe
            180                 185                 190

Gln Leu Gly Pro Asn Asn Arg Ser Cys Val Asp Val Asn Glu Cys Asp
            195                 200                 205

Met Gly Ala Pro Cys Glu Gln Arg Cys Phe Asn Ser Tyr Gly Thr Phe
        210                 215                 220

Leu Cys Arg Cys His Gln Gly Tyr Glu Leu His Arg Asp Gly Phe Ser
225                 230                 235                 240
```

```
Cys Ser Asp Ile Asp Glu Cys Ser Tyr Ser Ser Tyr Leu Cys Gln Tyr
                245                 250                 255

Arg Cys Val Asn Glu Pro Gly Arg Phe Ser Cys His Cys Pro Gln Gly
            260                 265                 270

Tyr Gln Leu Leu Ala Thr Arg Leu Cys Gln Asp Ile Asp Glu Cys Glu
        275                 280                 285

Ser Gly Ala His Gln Cys Ser Glu Ala Gln Thr Cys Val Asn Phe His
    290                 295                 300

Gly Gly Tyr Arg Cys Val Asp Thr Asn Arg Cys Val Glu Pro Tyr Ile
305             310                 315                 320

Gln Val Ser Glu Asn Arg Cys Leu Cys Pro Ala Ser Asn Pro Leu Cys
                325                 330                 335

Arg Glu Gln Pro Ser Ser Ile Val His Arg Tyr Met Thr Ile Thr Ser
            340                 345                 350

Glu Arg Ser Val Pro Ala Asp Val Phe Gln Ile Gln Ala Thr Ser Val
        355                 360                 365

Tyr Pro Gly Ala Tyr Asn Ala Phe Gln Ile Arg Ala Gly Asn Ser Gln
    370                 375                 380

Gly Asp Phe Tyr Ile Arg Gln Ile Asn Asn Val Ser Ala Met Leu Val
385             390                 395                 400

Leu Ala Arg Pro Val Thr Gly Pro Arg Glu Tyr Val Leu Asp Leu Glu
                405                 410                 415

Met Val Thr Met Asn Ser Leu Met Ser Tyr Arg Ala Ser Ser Val Leu
            420                 425                 430

Arg Leu Thr Val Phe Val Gly Ala Tyr Thr Phe
        435                 440

(2) INFORMATION FOR SEQ ID NO:2:

(i) SEQUENCE CHARACTERISTICS:
        (A) LENGTH: 2018 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT13
        (B) CLONE: 2786449

(xi) SEQUENCE DESCRIPTION: SEQ ID NO:2:

GGTGCGAGGA GGTCGAGGAG GCGCCTTGGC ACCCGACTCT GGCATCCCGC ACGTCCGACA      60

TCAGCCCTGC CCTCCTTCTC AGGGGCTTCC ATTCATTTTG TGCCAAAAGG GAACTGCCGC     120

CCGTCCGTCT GCCCGCAGGC ATTGCCCAAG CCAGCCGAGC CGCCAGAGCC GCGGGCCGCG     180

GGGGTGTCGC GGGCCCAACC CCAGGATGCT CCCCTGCGCC TCCTGCCTAC CCGGGTCTCT     240

ACTGCTCTGG GCGCTGCTAC TGTTGCTCTT GGGATCAGCT TCTCCTCAGG ATTCTGAAGA     300

GCCCGACAGC TACACGGAAT GCACAGATGG CTATGAGTGG GACCCAGACA GCCAGCACTG     360

CCGGGATGTC AACGAGTGTC TGACCATCCC TGAGGCCTGC AAGGGGGAAA TGAAGTGCAT     420

CAACCACTAC GGGGGCTACT TGTGCCTGCC CCGCTCCGCT GCCGTCATCA ACGACCTACA     480

TGGCGAGGGA CCCCCGCCAC CAGTGCCTCC CGCTCAACAC CCCAACCCCT GCCCACCAGG     540

CTATGAGCCC GACGATCAGG ACAGCTGTGT GGATGTGGAC GAGTGTGCCC AGGCCCTGCA     600

CGACTGTCGC CCCAGCCAGG ACTGCCATAA CTTGCCTGGC TCCTATCAGT GCACCTGCCC     660

TGATGGTTAC CGCAAGATCG GGCCCGAGTG TGTGGACATA GACGAGTGCC GCTACCGCTA     720

CTGCCAGCAC CGCTGCGTGA ACCTGCCTGG CTCCTTCCGC TGCCAGTGCG AGCCGGGCTT     780
```

-continued

```
CCAGCTGGGG CCTAACAACC GCTCCTGTGT TGATGTGAAC GAGTGTGACA TGGGGGCCCC      840

ATGCGAGCAG CGCTGCTTCA ACTCCTATGG GACCTTCCTG TGTCGCTGCC ACCAGGGCTA      900

TGAGCTGCAT CGGGATGGCT TCTCCTGCAG TGATATTGAT GAGTGTAGCT ACTCCAGCTA      960

CCTCTGTCAG TACCGCTGCG TCAACGAGCC AGGCCGTTTC TCCTGCCACT GCCCACAGGG     1020

TTACCAGCTG CTGGCCACAC GCCTCTGCCA AGACATTGAT GAGTGTGAGT CTGGTGCGCA     1080

CCAGTGCTCC GAGGCCCAAA CCTGTGTCAA CTTCCATGGG GGCTACCGCT GCGTGGACAC     1140

CAACCGCTGC GTGGAGCCCT ACATCCAGGT CTCTGAGAAC CGCTGTCTCT GCCCGGCCTC     1200

CAACCCTCTA TGTCGAGAGC AGCCTTCATC CATTGTGCAC CGCTACATGA CCATCACCTC     1260

GGAGCGGAGC GTGCCCGCTG ACGTGTTCCA GATCCAGGCG ACCTCCGTCT ACCCCGGTGC     1320

CTACAATGCC TTTCAGATCC GTGCTGGAAA CTCGCAGGGG GACTTTTACA TTAGGCAAAT     1380

CAACAACGTC AGCGCCATGC TGGTCCTCGC CCGGCCGGTG ACGGGCCCCC GGGAGTACGT     1440

GCTGGACCTG GAGATGGTCA CCATGAATTC CCTCATGAGC TACCGGGCCA GCTCTGTACT     1500

GAGGCTCACC GTCTTTGTAG GGGCCTACAC CTTCTGAGGA GCAGGAGGGA GCCACCCTCC     1560

CTGCAGCTAC CCTAGCTGAG GAGCCTGTTG TGAGGGGCAG AATGAGAAAG GCAATAAAGG     1620

GAGAAAGAAA GTCCTGGTGG CTGAGGTGGG CGGGTCACAC TGCAGGAAGC CTCAGGCTGG     1680

GGCAGGGTGG CACTTGGGGG GGCAGGCCAA GTTCACCTAA ATGGGGGTCT CTATATGTTC     1740

AGGCCCAGGG GCCCCCATTG ACAGGAGCTG GGAGCTCTGC ACCACGAGCT TCAGTCACCC     1800

CGAGAGGAGA GGAGGTAACG AGGAGGGCGG ACTCCAGGCC CCGGCCCAGA GATTTGGACT     1860

TGGCTGGCTT GCAGGGGTCC TAAGAAACTC CACTCTGGAC AGCGCCAGGA GGCCCTGGGT     1920

TCCATTCCTA ACTCTGCCTC AAACTGTACA TTTGGATAAG CCCTAGTAGT TCCCTGGGCC     1980

TGTTTTTCTA TAAAACGAGG CAACTGGAAA AAAAAAA                             2018
```

(2) INFORMATION FOR SEQ ID NO:3:

(i) SEQUENCE CHARACTERISTICS:
    (A) LENGTH: 387 amino acids
    (B) TYPE: amino acid
    (C) STRANDEDNESS: single
    (D) TOPOLOGY: linear (vii) IMMEDIATE SOURCE:
    (A) LIBRARY: GenBank
    (B) CLONE: 458228

(xi) SEQUENCE DESCRIPTION: SEQ ID NO:3:

```
Met Ala Thr Ser Gly Val Leu Pro Gly Gly Gly Phe Val Ala Ser Ala
 1               5                  10                  15

Ala Ala Val Ala Gly Pro Glu Met Gln Thr Gly Arg Asn Asn Phe Val
                20                  25                  30

Ile Arg Arg Asn Pro Ala Asp Pro Gln Arg Ile Pro Ser Asn Pro Ser
            35                  40                  45

His Arg Ile Gln Cys Ala Ala Gly Tyr Glu Gln Ser Glu His Asn Val
        50                  55                  60

Cys Gln Asp Ile Asp Glu Cys Thr Ala Gly Thr His Asn Cys Arg Ala
65                  70                  75                  80

Asp Gln Val Cys Ile Asn Leu Arg Gly Ser Phe Ala Cys Gln Cys Pro
                85                  90                  95

Pro Gly Tyr Gln Lys Arg Gly Glu Gln Cys Val Asp Ile Asp Glu Cys
               100                 105                 110

Thr Ile Pro Pro Tyr Cys His Gln Arg Cys Val Asn Thr Pro Gly Ser
           115                 120                 125
```

```
Phe Tyr Cys Gln Cys Ser Pro Gly Phe Gln Leu Ala Ala Asn Asn Tyr
    130             135                 140

Thr Cys Val Asp Ile Asn Glu Cys Asp Ala Ser Asn Gln Cys Ala Gln
145             150                 155                 160

Gln Cys Tyr Asn Ile Leu Gly Ser Phe Ile Cys Gln Cys Asn Gln Gly
            165             170                 175

Tyr Glu Leu Ser Ser Asp Arg Leu Asn Cys Glu Asp Ile Asp Glu Cys
            180             185                 190

Arg Thr Ser Ser Tyr Leu Cys Gln Tyr Gln Cys Val Asn Glu Pro Gly
        195                 200             205

Lys Phe Ser Cys Met Cys Pro Gln Gly Tyr Gln Val Val Arg Ser Arg
    210             215                 220

Thr Cys Gln Asp Ile Asn Glu Cys Glu Thr Thr Asn Glu Cys Arg Glu
225             230             235                     240

Asp Glu Met Cys Trp Asn Tyr His Gly Gly Phe Arg Cys Tyr Pro Arg
            245             250                 255

Asn Pro Cys Gln Asp Pro Tyr Ile Leu Thr Pro Glu Asn Arg Cys Val
            260             265             270

Cys Pro Val Ser Asn Ala Met Cys Arg Glu Leu Pro Gln Ser Ile Val
        275             280             285

Tyr Lys Tyr Met Ser Ile Arg Ser Asp Arg Ser Val Pro Ser Asp Ile
    290             295             300

Phe Gln Ile Gln Ala Thr Thr Ile Tyr Ala Asn Thr Ile Asn Thr Phe
305             310             315                 320

Arg Ile Lys Ser Gly Asn Glu Asn Gly Glu Phe Tyr Leu Arg Gln Thr
            325             330                 335

Ser Pro Val Ser Ala Met Leu Val Leu Val Lys Ser Leu Ser Gly Pro
            340             345             350

Arg Glu His Ile Val Asp Leu Glu Met Leu Thr Val Ser Ser Ile Gly
        355             360             365

Thr Phe Arg Thr Ser Ser Val Leu Arg Leu Thr Ile Ile Val Gly Pro
    370             375             380

Phe Ser Phe
385
```